US00PP28447P3

(12) United States Plant Patent
Lannes

(10) Patent No.: US PP28,447 P3
(45) Date of Patent: Sep. 26, 2017

(54) ***MANDEVILLA* PLANT NAMED 'LANFLORIDA'**

(50) Latin Name: *Mandevilla×amabilis×Mandevilla boliviensis*
Varietal Denomination: Lanflorida

(71) Applicant: D.H.M. INNOVATION S.A.S., Malause (FR)

(72) Inventor: Robert Lannes, Malause (FR)

(73) Assignee: D.H.M. Innovation S.A.S., Malause (FR)

( * ) Notice: Subject to any disclaimer, the term of this patent is extended or adjusted under 35 U.S.C. 154(b) by 32 days.

(21) Appl. No.: 14/998,345

(22) Filed: Jan. 4, 2016

(65) Prior Publication Data
US 2017/0196137 P1 Jul. 6, 2017

(51) Int. Cl.
*A01H 5/02* (2006.01)

(52) U.S. Cl.
USPC ..... Plt./232

(58) Field of Classification Search
USPC ..... Plt./232
See application file for complete search history.

*Primary Examiner* — Keith Robinson
(74) *Attorney, Agent, or Firm* — C. A. Whealy

(57) ABSTRACT

A new and distinct cultivar of *Mandevilla* plant named 'Lanflorida', characterized by its upright and twining plant habit; moderately vigorous to vigorous growth habit; glossy dark green-colored leaves; freely flowering habit; and white-colored flowers with red purple-colored centers.

2 Drawing Sheets

Botanical designation: *Mandevilla×amabilis×Mandevilla boliviensis.*

Cultivar denomination: 'LANFLORIDA'.

BACKGROUND OF THE INVENTION

The present invention relates to a new and distinct cultivar of *Mandevilla* plant, botanically known as *Mandevilla×amabilis×Mandevilla boliviensis* and hereinafter referred to by the name 'Lanflorida'.

The new *Mandevilla* plant is a product of a planned breeding program conducted by the Inventor in Malause, France. The objective of the breeding program is to create new *Mandevilla* plants with good plant habit and numerous attractive flowers.

The new *Mandevilla* plant originated from a cross-pollination conducted by the Inventor in Malause, France in 2009 of *Mandevilla×amabilis×Mandevilla boliviensis* 'Sunmandeho', disclosed in U.S. Plant Pat. No. 11,556, as the female, or seed, parent with a proprietary selection of *Mandevilla×amabilis×Mandevilla boliviensis* identified as code number Si-06-850-13, not patented, as the male, or pollen, parent. The new *Mandevilla* plant was discovered and selected by the Inventor as a single flowering plant from within the progeny of the stated cross-pollination in a controlled greenhouse environment in Malause, France in 2013.

Asexual reproduction of the new *Mandevilla* plant by cuttings in a controlled greenhouse environment in Malause, France, since July, 2014 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Lanflorida'. These characteristics in combination distinguish 'Lanflorida' as a new and distinct *Mandevilla* plant:

1. Upright and twining plant habit.
2. Moderately vigorous to vigorous growth habit.
3. Glossy dark green-colored leaves.
4. Freely flowering habit.
5. White-colored flowers with red purple-colored centers.

Plants of the new *Mandevilla* can be compared to plants of the female parent, 'Sunmandeho'. Plants of the new *Mandevilla* differ primarily from plants of 'Sunmandeho' in plant habit as plants of 'Sunmandeho' have a climbing type habit whereas plants of the new *Mandevilla* do not have a climbing type habit.

Plants of the new *Mandevilla* can be compared to plants of the male parent selection. Plants of the new *Mandevilla* differ primarily from plants of the male parent selection in flower color as plants of the male parent selection have pink-colored flowers.

Plants of the new *Mandevilla* can also be compared to plants of *Mandevilla sanderi* 'Lannorthcarolina', disclosed in U.S. Plant Pat. No. 25,851. In side-by-side comparisons conducted in Malause, France, plants of the new *Mandevilla* differed primarily from plants 'Lannorthcarolina' in flower color as plants of 'Lannorthcarolina' have pink-colored flowers.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Lanflorida' grown in a container.

The photograph on the second sheet is a close-up view of a typical flower of 'Lanflorida'.

DETAILED BOTANICAL DESCRIPTION

The aforementioned photographs and following observations, measurements and values describe plants grown during the spring and early summer in 17-cm containers in polyethylene-covered greenhouse in Malause, France and under cultural practices typical of commercial *Mandevilla* production. During the production of the plants, day temperatures ranged from 15° C. to 26° C. and night temperatures ranged from 14° C. to 15° C. Plants were six months old when the photographs and description were taken. In the following description, color references are made to The Royal Horticultural Society Colour Chart, 2007 Edition, except where general terms of ordinary dictionary significance are used.

Botanical classification: *Mandevilla×amabilis×Mandevilla boliviensis* 'Lanflorida'.

Parentage:

*Female, or seed, parent.*—*Mandevilla×amabilis×Mandevilla boliviensis* 'Sunmandeho', disclosed in U.S. Plant Pat. No. 11,556.

*Male, or pollen, parent.*—Proprietary selection of *Mandevilla×amabilis×Mandevilla boliviensis* identified as code number Si-06-850-13, not patented.

Propagation:

*Type.*—By vegetative cuttings.

*Time to initiate roots, summer.*—About two weeks at temperatures about 23° C. to 30° C.

*Time to initiate roots, winter.*—About three weeks at temperatures about 23° C. to 25° C.

*Time to produce a rooted young plant, summer.*—About five to six weeks at temperatures about 23° C. to 30° C.

*Time to produce a rooted young plant, winter.*—About six to eight weeks at temperatures about 23° C. to 25° C.

*Root description.*—Fibrous, fine; typically light yellowish white in color, actual color of the roots is dependent on substrate composition, water quality, fertilizers, substrate temperature and physiological age of roots.

*Rooting habit.*—Freely branching; medium density.

Plant description:

*Plant and growth habit.*—Upright and twining plant habit; narrowly upright; moderately vigorous to vigorous growth habit.

*Plant height.*—About 62 cm.

*Plant diameter* (*spread*).—About 35.2 cm.

*Lateral branch description.*—Branching habit: Moderately freely branching habit with about three lateral branches developing per plant; pinching enhances lateral branch development. Length: About 60.5 cm. Diameter: About 3.5 mm. Internode length: About 9 cm. Strength: Strong. Texture and luster: Smooth, glabrous; moderately glossy. Color, developing: Close to 144B. Color, developed: Close to N199B and N199C.

Leaf description:

*Arrangement.*—Opposite, simple.

*Length.*—About 13.2 cm.

*Width.*—About 7.5 cm.

*Shape.*—Ovate to oblong.

*Apex.*—Short apiculate.

*Base.*—Truncate to cordate.

*Margin.*—Entire.

*Texture and luster, upper and lower surfaces.*—Smooth, glabrous; glossy.

*Venation pattern.*—Pinnate, reticulate.

*Color.*—Developing leaves, upper surface: Darker than 143A. Developing leaves, lower surface: Close to 146A to 146B. Full expanded leaves, upper surface: Darker than between N137A and 147A; venation, close to 146C. Fully expanded leaves, lower surface: Close to between 146B and 147B; venation, close to 145A.

*Petiole length.*—About 9 mm.

*Petiole diameter.*—About 3.5 mm to 4 mm.

*Petiole strength.*—Moderately strong to strong.

*Petiole texture, upper and lower surfaces.*—Smooth, glabrous.

*Petiole color, upper and lower surfaces.*—Close to 144B.

Flower description:

*Flower type and flowering habit.*—Single salverform flowers arranged in terminal and axillary cymes; flowers star-shaped and face mostly upright and outwardly; freely flowering habit with about twelve flowers developing per inflorescence and about 100 flowers developing per plant during the flowering season.

*Natural flowering season.*—Plants flower continuously from early summer into the autumn in France.

*Flower longevity on the plant.*—About seven days; flowers not persistent.

*Fragrance.*—Faint; sweet and pleasant.

*Inflorescence height.*—About 33.5 cm.

*Inflorescence diameter.*—About 12.2 cm.

*Flower buds.*—Length: About 6.5 cm. Diameter: About 1.5 cm. Shape: Narrowly obovate. Color: Close to 155C; towards the base, close to 144C to 144D; towards the apex, close to 157C to 157D.

*Flowers.*—Appearance: Flared trumpet, corolla fused and five-parted. Diameter: About 9 cm. Depth (length): About 7 cm. Tube length: About 4.2 cm.

*Corolla.*—Quantity and arrangement: Five petals arranged in a single whorl and fused towards the base. Petal length: About 8.9 cm. Petal width: About 3.7 cm. Petal shape and appearance: Roughly spatulate; lower 47.5% of the petal is fused into a tube; free part, slightly reflexed and somewhat twisting. Petal apex: Non-symmetrically acute. Petal margin: Entire. Petal texture and luster, upper surface: Smooth, glabrous; moderately velvety; matte. Petal texture and luster, lower surface: Smooth, glabrous; very slightly glossy. Throat and tube texture: Smooth, glabrous. Color: Petal, when opening and fully opened, upper surface: Close to NN155D; towards the throat, close to 68A; throat, close to 1A; at the base of the throat, close to 145B. Petal, when opening and fully opened, lower surface: Close to NN155D; towards the tube, close to 68A (from upper surface); tube, close to 145C; at the base of the tube, close to 144C.

*Corona*.—Quantity and arrangement: Five sepals arranged in a single whorl. Sepal length: About 1 cm. Sepal width: About 2 mm. Sepal shape: Lanceolate. Sepal apex: Narrowly acuminate. Sepal base: Roughly truncate. Sepal margin: Entire. Sepal texture and luster, upper and lower surfaces: Smooth, glabrous; matte. Sepal color: Immature, upper and lower surfaces: Close to N144D; towards the apex, tinged with close to 180B to 180C. Mature, upper and lower surfaces: Close to N144D; towards the apex, tinged with close to 180B.

*Peduncles*.—Length: About 30.7 cm. Diameter: About 3 mm. Texture: Smooth, glabrous. Strength: Strong. Color: Close to 144B.

*Pedicels*.—Length: About 1.9 cm. Diameter: About 2 mm. Texture: Smooth, glabrous. Strength: Strong. Color: Close to 144C.

*Reproductive organs*.—Stamens: Quantity and arrangement: Typically five; basifixed; anthers connivent. Filament length: About 1 mm. Anther shape: Narrowly oblong. Anther length: About 8 mm. Anther color: Close to 160C. Pollen amount: None observed. Pistils: Quantity: Typically one. Pistil length: About 2 cm. Style length: About 1.7 cm. Style color: Close to 157D. Stigma shape: Sagittate. Stigma color: Close to 143C. Ovary color: Close to 144C.

*Seeds and fruits*.—Seed and fruit production have not been observed on plants of the new *Mandevilla*.

Disease & pest resistance: Plants of the new *Mandevilla* have not been noted to be resistant to pathogens and pests common to *Mandevilla* plants.

Temperature tolerance: Plants of the new *Mandevilla* have been observed to tolerate high temperatures of about 40° C. and to be hardy to USDA Hardiness Zone 9.

It is claimed:

1. A new and distinct *Mandevilla* plant named 'Lanflorida' as illustrated and described.

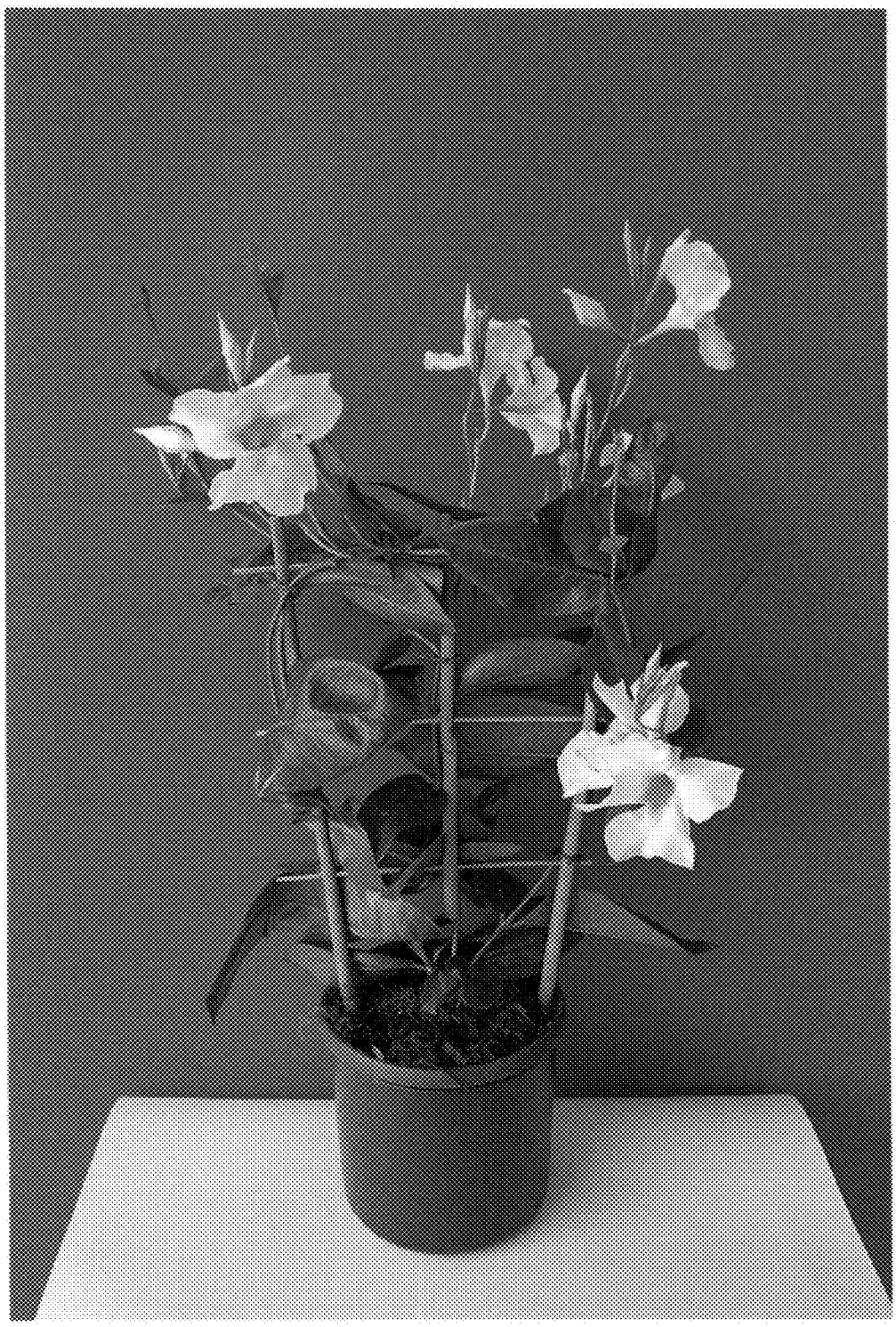

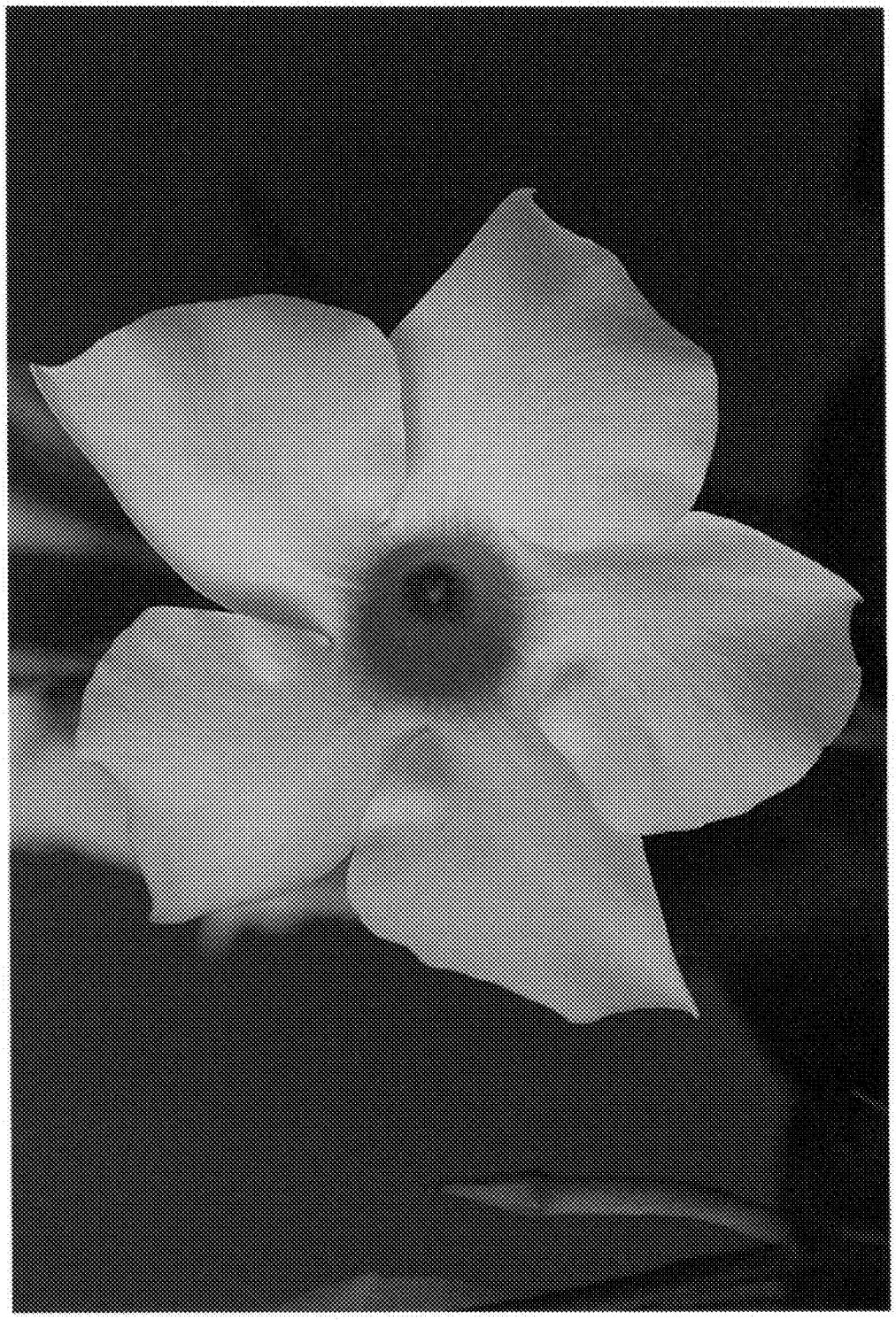

* * * * *